US00PP36799P2

(12) United States Plant Patent
Nontaswatsri

(10) Patent No.: US PP36,799 P2
(45) Date of Patent: Jul. 1, 2025

(54) ***CURCUMA* PLANT NAMED 'Maejo Pink Pearl'**

(50) Latin Name: ***Curcuma* hybrid**
Varietal Denomination: Maejo Pink Pearl

(71) Applicant: Maejo University, Chiang Mai (TH)

(72) Inventor: Chalermsri Nontaswatsri, Chiang Mai (TH)

(73) Assignee: Maejo University (TH)

( * ) Notice: Subject to any disclaimer, the term of this patent is extended or adjusted under 35 U.S.C. 154(b) by 0 days.

(21) Appl. No.: 18/759,560

(22) Filed: Jun. 28, 2024

(51) Int. Cl.
*A01H 5/02* (2018.01)
*A01H 6/00* (2018.01)

(52) U.S. Cl.
USPC ..... Plt./421
CPC ..... *A01H 6/00* (2018.05)

(58) Field of Classification Search
USPC ..... Plt./421
CPC ..... A01H 5/02
See application file for complete search history.

*Primary Examiner* — Kent L Bell

(57) ABSTRACT

A new and distinct cultivar of *Curcuma* plant named 'Maejo Pink Pearl' is described, characterized by light-yellow flowers with a light-purple stomata and pink lower bracts with a brown stripe. The new variety is a *Curcuma*, normally used as an ornamental garden or landscape plant.

4 Drawing Sheets

Latin name of the genus and species: *Curcuma* hybrid.
Variety denomination: 'MAEJO PINK PEARL'.

BACKGROUND OF THE INVENTION

The new cultivar, *Curcuma* 'Maejo Pink Pearl', is a product of a planned breeding program by the inventor. 'Maejo Pink Pearl' is the result of the crossing of the seed parent, an unnamed, unpatented *Curcuma alismatifolia* x *Curcuma aurantiaca* plant, and the pollen parent, the unpatented *Curcuma* 'Big Red' plant. The crossing occurred during October 2016, at a nursery in Chiang Mai Province, Thailand. 'Maejo Pink Pearl' was selected as an interesting new cultivar at the same location in October of 2018.

The first asexual propagation of 'Maejo Pink Pearl' was performed in October of 2018 by tissue culture at the same nursery in Chiang Mai Province, Thailand, and has been found to retain its distinctive characteristics through successive asexual propagations.

SUMMARY OF THE INVENTION

The cultivar 'Maejo Pink Pearl' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Maejo Pink Pearl'. These characteristics in combination distinguish 'Maejo Pink Pearl' as a new and distinct *Curcuma* cultivar:

1. Light-yellow flowers with a light-purple stomata.
2. Large inflorescence.
3. Pink lower bracts with a brown stripe.

PARENT COMPARISONS

Plants of the new cultivar 'Maejo Pink Pearl' are similar to plants of the seed parent in most horticultural characteristics. However, plants of the new cultivar 'Maejo Pink Pearl' differ in the following:

1. Plants of the new variety are taller than plants of the seed parent.
2. Leaves of the new variety are smaller and narrower than leaves of the seed parent.
3. Flower color of the new variety is light-yellow with a light-purple stomata. Flower color of the seed parent is white.
4. Peduncles of the new variety are longer than peduncles of the seed parent.
5. Inflorescence of the new variety is larger than the inflorescence of the seed parent.
6. Lower bracts of the new variety are pink with a brown stripe, while lower bracts of the seed parent are green with a brown stripe.

Plants of the new cultivar 'Maejo Pink Pearl' are similar to plants of the pollen parent in most horticultural characteristics. However, plants of the new cultivar 'Maejo Pink Pearl' differ in the following:

1. Plants of the new variety are larger than plants of the pollen parent.
2. Leaves of the new variety are larger and broader than leaves of the pollen parent.
3. Flower color of the new variety is light-yellow with a light-purple stomata. Flower color of the pollen parent is white with a deep purple lip.
4. Peduncles of the new variety are shorter than peduncles of the pollen parent.
5. Inflorescence of the new variety is larger than the inflorescence of the pollen parent.
6. Lower bracts of the new variety are pink with a brown stripe, while lower bracts of the pollen parent are green.

COMMERCIAL COMPARISON

'Maejo Pink Pearl' can be compared to the commercial variety *Curcuma sieboldii* 'Sawasdee-Venus', unpatented. Plants of the new variety are similar to 'Sawasdee-Venus' in most horticultural characteristics, however, 'Maejo Pink Pearl' differs in the following:

1. Peduncles of the new variety are longer than peduncles of this comparator.
2. Inflorescence of the new variety is larger than the inflorescence of this comparator.
3. Lower bracts of the new variety are pink with a brown stripe, while lower bracts of this comparator are green with a brown stripe.
4. Leaves of the new variety are smaller and narrower than leaves of this comparator.
5. Flower color of the new variety is light-yellow with a light-purple stomata, while the flower color of this comparator is pinkish-orange.
6. Plants of the new variety are taller than plants of this comparator.

BRIEF DESCRIPTION OF THE PHOTOGRAPHS

The accompanying photographs were taken using conventional techniques and although colors may appear different from actual colors due to light reflectance it is as accurate as possible by conventional photographic techniques. All photographs are of a plant of approximately 4 to 5 months of age.

DETAILED BOTANICAL DESCRIPTION

Figure 1:
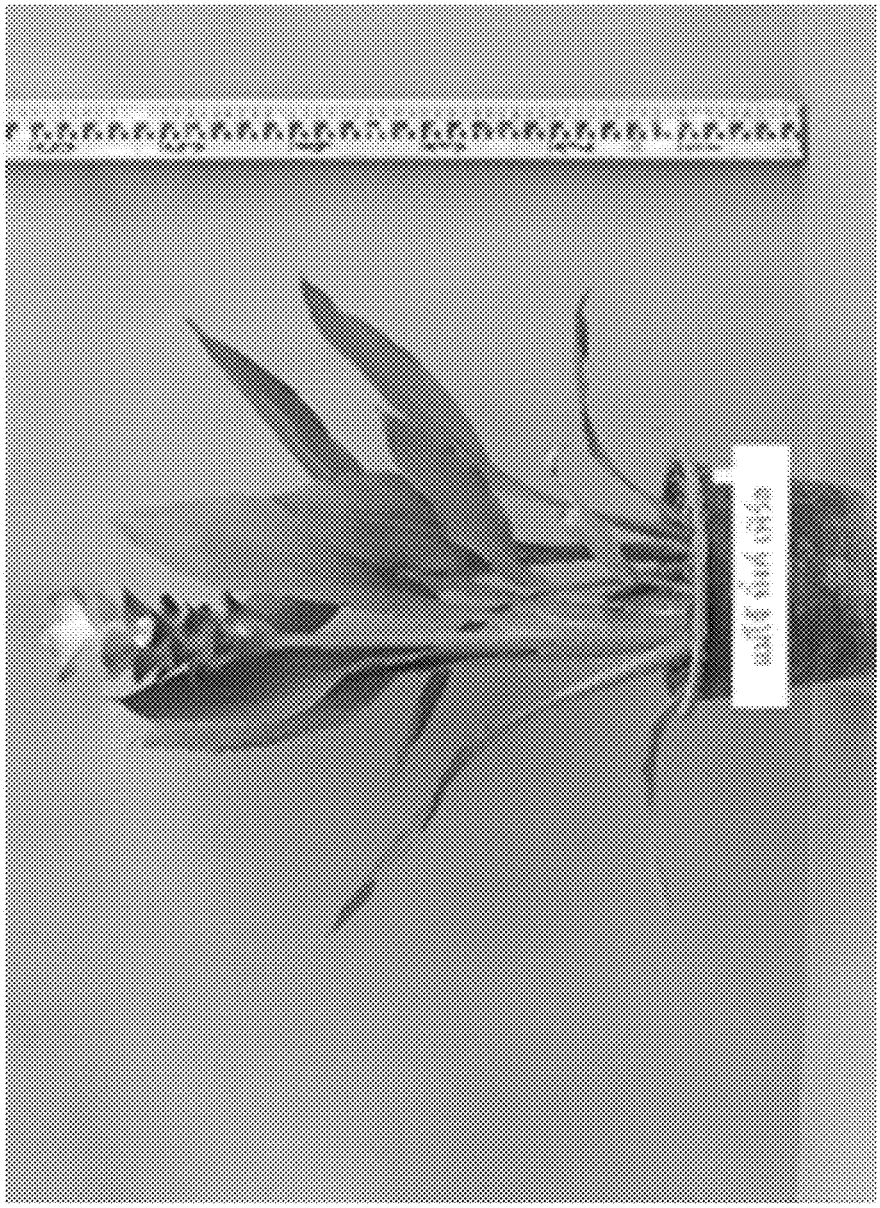
FIG. 1 illustrates a flowering plant of the new variety at approximately 4 to 5 months of age.
Figure 2:
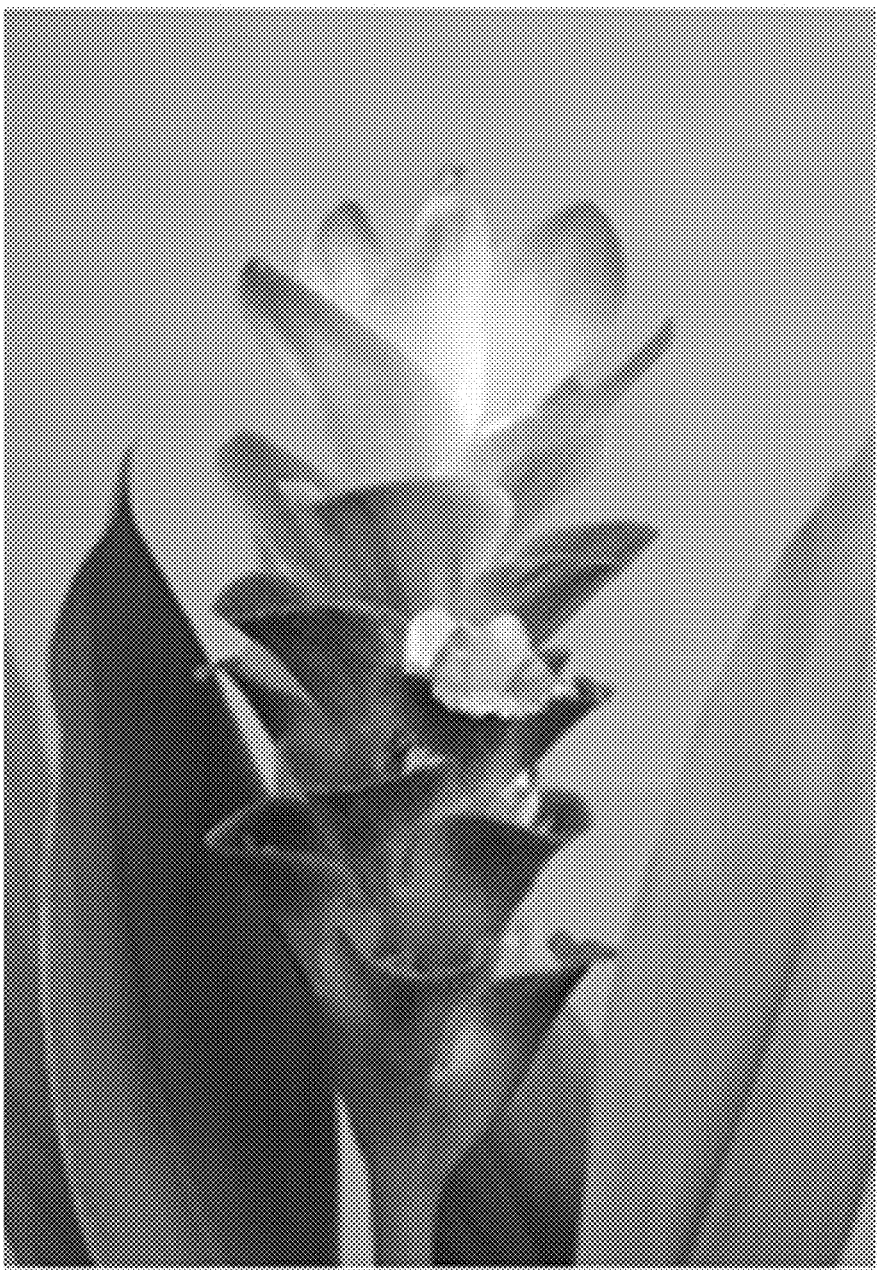
FIG. 2 is a close-up view of a typical inflorescence of the new variety.
Figure 3:
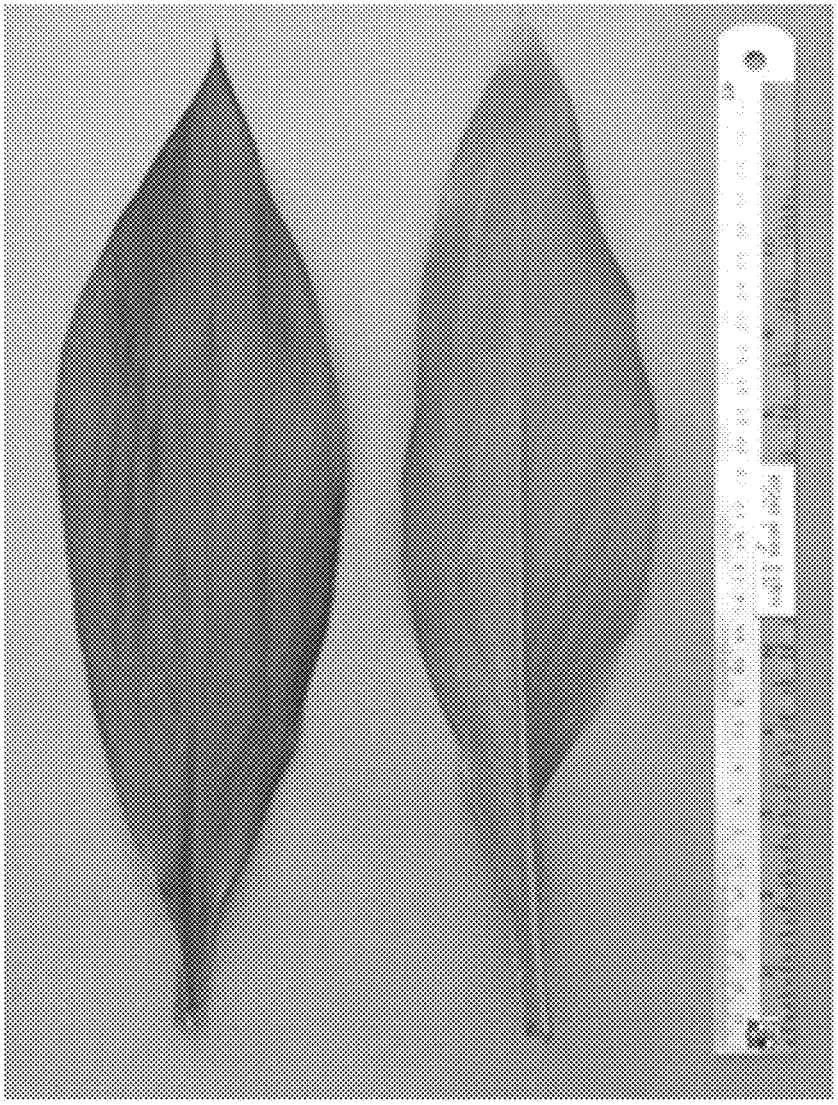
FIG. 3 is a close-up view of typical foliage of the new variety.
Figure 4:
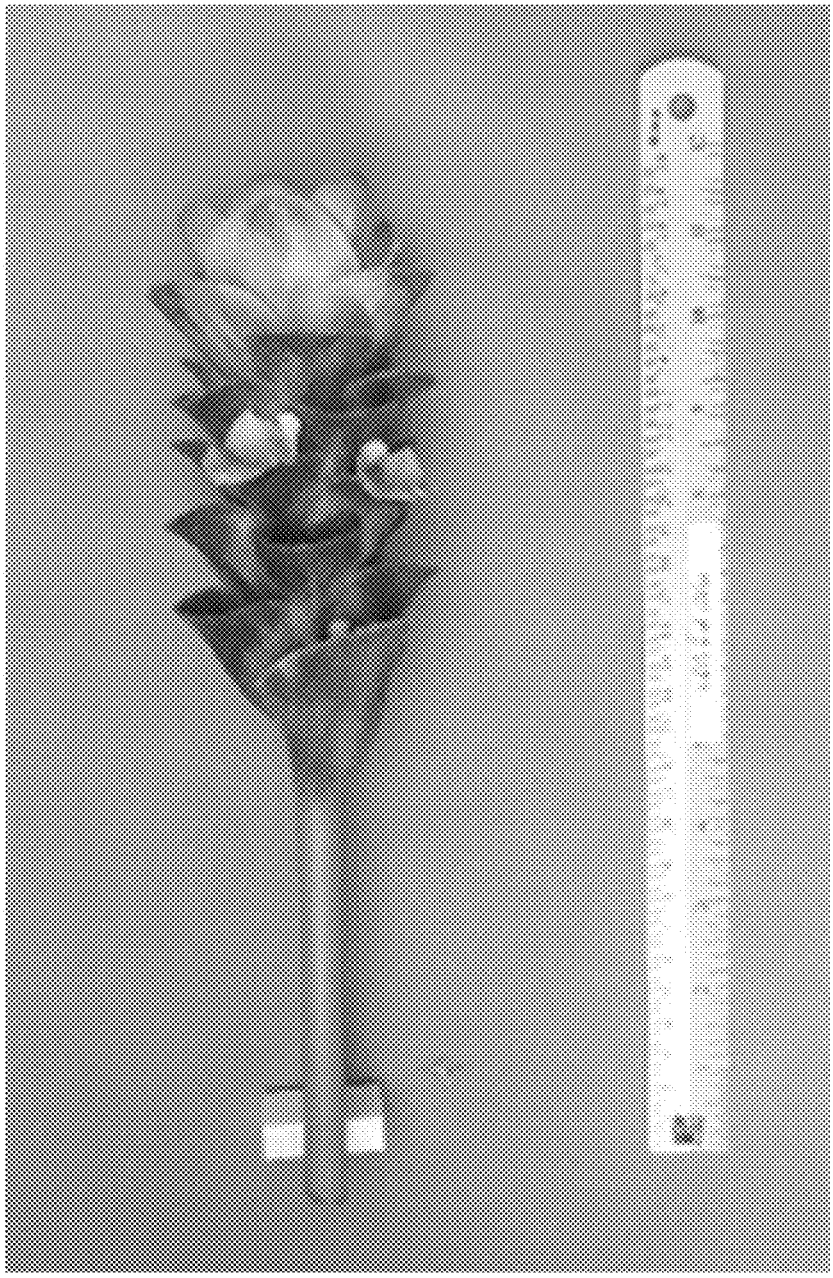
FIG. 4 is a close-up view of a typical inflorescence of the new variety, along with a ruler with centimeter units.

The following is a detailed description of the botanical characteristics of the new and distinct *Curcuma* 'Maejo Pink Pearl'. The detailed description was taken from a 2-year-old container grown plant in Chiang Mai Province, Thailand. All colors cited herein refer to The Royal Horticultural Society Colour Chart (R.H.S.), London, Sixth Edition. Where specific dimensions, sizes, colors, and other characteristics are given, it is to be understood that such characteristics are approximations or averages set forth as accurately as practicable.

Botanical classification: *Curcuma* 'Maejo Pink Pearl'.

PROPAGATION

Method: Tissue culture.

ROOTS

Description: Moderate density, 5 to 10 main roots per plant. White in color, not accurately measured with R.H.S. chart.

Rhizome description: 1 to 3 per plant. 1.5 to 3.0 cm in diameter. Cream in color, near RHS Yellow-White 158D. Length of Rhizome depends on the pot size as rhizomes will grow to the limit of the pot.

PLANT

Height: 46.4 cm.

Plant spread: 41.2 cm.

Pseudostem:

*Quantity.*—2 to 3 average.
*Width.*—4 cm.
*Length.*—12.2 cm.
*Color.*—RHS Green 143B.

FOLIAGE

Leaf:

*Arrangement.*—Broad and alternate.
*Length.*—Average 28.5 cm.
*Width.*—Average 8.1 cm.
*Shape.*—Elliptic.
*Apex.*—Acuminate.
*Base.*—Attenuate.
*Margin.*—Entire.
*Aspect.*—Initially upright, then about 45° from vertical.
*Texture.*—Top surface: Smooth, glabrous, matte. Bottom surface: Smooth, glabrous, matte.
*Color.*—Developing, upper side: RHS Green 138A. Developing, under side: RHS Green 138B. Fully expanded, upper side: RHS Green 137C. Fully expanded, under side: RHS Green 137C.
*Venation.*—Type: Pinnate and penninerved. Color: Near Green 143C upper and lower surfaces.
*Sheath.*—Length: 20 to 30 cm. Width: 5 to 10 cm. Texture: Glabrous. Color: Near RHS Green 137D.

FLOWER

Inflorescence:

*Arrangement.*—Dense and upright terminal spike inflorescences developing directly from the basal shoots with numerous showy flower bracts.
*Time to flower.*—In Thailand, plants begin flowering about 16 to 18 weeks after planting.
Inflorescence longevity.—About 1 month on the plant if plants are maintained in good substance.
*Quantity.*—1 to 3 per plant.
*Fragrance.*—None.
*Length.*—About 25.2 cm.
*Diameter.*—About 6.2 cm.

Flower bracts:

*Quantity.*—About 10 upper bracts and about 20 lower bracts per inflorescence.
*Length, upper bracts.*—About 4.4 cm.
*Width, upper bracts.*—About 3.5 cm.
*Length, lower bracts.*—About 5 cm.
*Width, upper bracts.*—About 4 cm.
*Shape, upper bracts.*—Elliptic.
*Shape, lower bracts.*—Shallow U-shaped.
*Apex, upper bracts.*—Acute.
*Apex, lower bracts.*—Obtuse.
*Base, all bracts.*—Fused.
*Margin, upper bracts.*—Entire.
*Margin, lower bracts.*—Entire, undulate.
*Texture, upper bracts.*—Upper and lower surfaces smooth, glabrous, slightly glossy.
*Texture, lower bracts.*—Upper and lower surfaces smooth, glabrous; moderately glossy.
*Color.*—Upper bracts, upper surface: RHS Greyed-Purple 186B; the apex; lower section strongly tinged with Yellow-Green 146D, base 146D. Lower bracts, upper surface: RHS Green 143C, apex Greyed-Red 178A. Upper bracts, lower surface: RHS Greyed-Purple 186B; the apex; lower section strongly tinged with Yellow-Green 146D, base 146D. Lower bracts, lower surface: RHS Green 143C mixed with 178A.

Flowers:

*Flowers per inflorescence.*—60-100 flowers.

*Lastingness of an individual flower.*—1-2 days (Continuity of flowering: around 1 month).

*Flower shape.*—Zygomorphic with three petals fused towards the base; dorsal petal (labellum) is conspicuous and two smaller lateral petals; calyx with three sepals fused at the base.

*Flower length.*—Approx. 4 cm.

*Flower diameter.*—Approx. 2 cm.

Petals:

*Petals per flower.*—Zygomorphic with three petals fused towards the base; dorsal petal (labellum) is conspicuous and two smaller lateral petals.

*Petal shape.*—labellum.

*Petal length.*—1-1.5 cm.

*Petal width.*—1-1.5 cm.

*Petal apex.*—Obtuse.

*Petal margin.*—Absent.

*Petal base.*—Three petals fused towards the base.

*Dorsal petal color.*—Upper surface: Purple N75B and N75C with stripes Purple 77A and Yellow 2B; Lower surface: Yellow 2D.

*Lateral petal color.*—Upper surface Yellow 2C; Lower surface Yellow 2D.

Sepals:

*Sepal number.*—3.

*Sepal shape.*—Lanceolate.

*Sepal length.*—1.5 cm.

*Sepal width.*—0.5 cm.

*Sepal apex.*—Acute.

*Sepal margin.*—Absent.

*Sepal base.*—Obtuse.

*Sepal color, upper and lower surfaces.*—Pearl pink both upper and lower surfaces.

Peduncle:

*Peduncle length.*—10-15 cm.

*Peduncle diameter.*—0.7-1 cm.

*Peduncle texture.*—Smooth, waxy.

*Peduncle color.*—Green 137B.

REPRODUCTIVE ORGANS

Pistils:

*Pistil number.*—1.

*Pistil length.*—About 4 cm.

*Style length.*—About 3 cm.

*Style diameter.*—About 2 mm.

*Style color.*—Yellow-Green N144D.

*Stigma shape.*—Club-shaped.

*Stigma diameter.*—About 1.5 mm.

*Stigma color.*—RHS Yellow-Green N144C.

*Ovary color.*—RHS Yellow-Green N144D.

Stamens:

*Stamen number.*—2 per flower.

*Filament length.*—About 1.2 cm.

*Filament diameter.*—About 2 mm.

*Filament color.*—RHS Yellow-Green 154D.

*Anther length.*—About 5 mm.

*Anther width.*—About 2 mm.

*Anther shape.*—Narrowly oblong.

*Anther color.*—RHS Yellow-Green 154C.

*Pollen amount.*—None.

OTHER CHARACTERISTICS

Fruit/seed: None.

Disease/pest resistance: Neither resistance nor susceptibility to the normal pests and diseases of *Curcuma* has been observed.

Temperature tolerance: 20° to 40° C. or tropical climate conditions.

Drought tolerance: None.

What is claimed is:

1. A new and distinct cultivar of *Curcuma* plant named 'Maejo Pink Pearl', substantially as illustrated and described herein.

* * * * *